United States Patent [19]

Newton et al.

[11] Patent Number: 5,547,918
[45] Date of Patent: Aug. 20, 1996

[54] BIOCIDAL AND AGROCHEMICAL SUSPENSIONS COMPRISING A STRUCTURED SURFACTANT WITH AN OIL COMPONENT

[76] Inventors: Jill E. Newton, 27 Silverdale Gardens, Stourbridge; Richard M. Clapperton, 9 Woodhouse Orchard, Stourbridge; William J. Nicholson, 117 Nimmings Rd., Halesowen, all of United Kingdom

[21] Appl. No.: 457,170

[22] Filed: Jun. 1, 1995

Related U.S. Application Data

[63] Continuation of Ser. No. 385,749, Feb. 8, 1995, abandoned, which is a continuation of Ser. No. 246,938, May 20, 1994, abandoned, which is a continuation of Ser. No. 84,775, Jun. 29, 1973, abandoned, which is a continuation of Ser. No. 826,076, Jan. 27, 1992, abandoned.

[30] Foreign Application Priority Data

Feb. 8, 1991 [GB] United Kingdom ................... 9102757

[51] Int. Cl.⁶ ..................................... A01N 25/30
[52] U.S. Cl. .......................... 504/116; 424/405; 514/786; 514/789; 514/975
[58] Field of Search ..................................... 504/116, 288, 504/304, 308, 342; 514/85, 383, 637, 784, 786, 787, 975; 71/DIG. 1; 424/405

[56] References Cited

U.S. PATENT DOCUMENTS

| | | | |
|---|---|---|---|
| 3,873,689 | 3/1975 | Frensch et al. | 71/DIG. 1 |
| 4,804,399 | 2/1989 | Albrecht et al. | 71/93 |
| 5,096,711 | 3/1992 | Dookhith et al. | 71/DIG. 1 |
| 5,139,152 | 8/1992 | Hodakowski et al. | 71/DIG. 1 |

FOREIGN PATENT DOCUMENTS

| | | |
|---|---|---|
| 495694 | 9/1950 | Belgium . |
| 0083437 | 7/1983 | European Pat. Off. . |
| 0253762 | 1/1988 | European Pat. Off. . |
| 0388239 | 9/1990 | European Pat. Off. . |
| 1438307 | 4/1966 | France . |
| 679399 | 9/1952 | United Kingdom . |
| 2123846 | 2/1984 | United Kingdom . |
| 2153380 | 8/1985 | United Kingdom . |
| 2123294 | 2/1994 | United Kingdom . |
| WO87/05778 | 10/1987 | WIPO . |

*Primary Examiner*—S. Mark Clardy

[57] ABSTRACT

A biocidal or agrochemical composition comprising particles or droplets of a substantially water-insoluble or sparingly-soluble biocidally-or agrochemically-active substance cosuspended, by an aqueous structured surfactant, with an aliphatic hydrocarbon or glyceride oil, wherein the weight ratio of said surfactant to said active substance is less than 20:1

23 Claims, No Drawings

BIOCIDAL AND AGROCHEMICAL SUSPENSIONS COMPRISING A STRUCTURED SURFACTANT WITH AN OIL COMPONENT

This application is a continuation of application Ser. No. 08/385,749, filed Feb. 8, 1995 (abandoned), which is a continuation of application Ser. No. 08/246,938, filed May 20, 1994 (abandoned), which is a continuation application of Ser. No. 08/084,775, filed Jun. 29, 1993 (abandoned), which is a continuation of application Ser. No. 07/826,076, filed Jan. 27, 1992 (abandoned).

The present invention provides a novel means of suspending relatively water-insoluble biocidal or agrochemical active substances in aqueous media without the need to employ environmentally harmful solvents. The term "agrochemical" is used herein broadly to cover chemicals that kill, entrap, repel or inhibit the growth or reproduction of unwanted organisms ("pests") or which protect or promote the healthy growth or reproduction of wanted organisms such as crops, ornamental plants, livestock and domestic animals, and which are useful in agriculture, horticulture, forestry, animal husbandry, agriculture, water treatment and land management, e.g. for application to fields, crops, orchards, livestock, gardens, woodland, hedgerows, parks, industrial estates, construction sites, airports, roads, railways, rivers, lakes, ponds, canals, irrigation and drainage works and the like.

Pests include vertebrate vermine such as rodents, rabbits and pigeons, invertebrates such as insects, mites, slugs, snails, nematodes, flatworms, millipedes and pathogenic protozoa, weeds, fungi, moulds, bryophites, lichens, algae, yeasts, bacteria and viruses.

"Biocidal and agrochemical active substances" include substances intended to kill, entrap, repel or to prevent or inhibit the growth or reproduction of any or all of the aforesaid pests. They also include growth promoters such as hormones, auxins, gibberellins, nutrients, trace elements for application to soil or crops and biocides for use in water treatment such as boiler water, process water, cooling water, oil field injection water, central heating and air conditioning systems, but excludes animal foodstuffs and veterinary preparations for internal administration.

A number of substantially water insoluble biocidal and agrochemical active substances, are used extensively for controlling pests and/or for promoting the healthy growth of crops and livestock. For this purpose it is usually necessary or preferred to apply them in a fluid and preferably a diluted form. This frequently requires that the active substances be formulated in a stable aqueous based concentrate suitable for dilution with water.

Hitherto the only practical approach to formulating many of the less water soluble agrochemicals has been to dissolve them in an organic water-immiscible solvent, usually an aromatic hydrocarbon such as xylene or isophorone, and emulsify the resulting organic solution in water. A major disadvantage of this method is that the solvents commonly used are undesirable ecologically and from the stand point of human safety. Only the lack of a practicable alternative means of formulating many agrochemicals has prevented more severe restrictions on the use of such solvents.

Other approaches to the problem of applying some of the less water soluble agrochemicals have included the formulation of wettable powders or dispersible granules, both of which present problems for the user of handling solids and dispensing them in liquid. Attempts have been made to prepare concentrated aqueous suspensions of agrochemicals, but these have generally suffered from poor stability leading to sedimentation on standing, high viscosity leading to difficulties in handling and diluting, and/or high cost due to the use of expensive dispersants and thickeners.

Our British Patent Application No. 89 06234 describes and claims a method of suspending relatively water-insoluble biocides and agrochemicals to form highly concentrated, stable, pourable, aqueous-based suspensions suitable for dilution with water prior to application, which method does not rely on the use of potentially harmful solvents. The use of structured surfactants is generally applicable to the preparation of stable suspensions of a wide range of insoluble or sparingly-soluble biocides and agrochemicals, including many that have hitherto only been available in organic solvents, or as wettable powders, or as unstable suspensions.

According to our aforesaid Patent Application, substantially water-insoluble or sparingly soluble biocides and agrochemicals may be suspended, at concentrations of 10 to 70% by weight or higher, in aqueous structured surfactant systems. The expression "structured surfactant system" refers to aqueous systems in which surfactants form mesophases comprising structures larger than conventional spherical micelies, which interact to confer thixotropic properties on the aqueous medium. The structures may be solid, mesophase or liquid and may be in the form of multi layered spherulites or lamellae discontinuously dispersed or emulsified in the system or forming weak reticular structures or of rods or discs. The size of the structures may typically lie within the range 0.01 to 200 microns, preferably 0.5 to 20 microns. Structured surfactant systems are usually formed by the interaction of surfactants with dissolved electrolyte salts or bases. Such systems are present in some liquid detergents and cleaning compositions and have been described, for instance, in GB-2,123,846 and GB-A-2,153, 380.

Use of structured surfactants to suspend agrochemicals offers a number of potential advantages. In many instances the activity and/or selectivity of the active material is increased. The structured surfactants are capable of suspending a wide range of particle sizes and may be adapted to a wide range of pH e.g. by appropriate choice of surfactant. The systems are generally obtainable in a shear stable form which facilitates wet milling.

It is known that aliphatic oils can enhance the performance of many water insoluble or sparingly soluble pesticides. We have now discovered that aliphatic oils such as paraffin oils or glyceride oils, e.g. vegetable oils, can be included in stable structured surfactant systems. The oil appears, unexpectedly to be incorporated into the mesophase structure. We believe, without wishing to be limited thereby, that the oil is included in the surfactant bilayers which characterise most structured surfactants. When oil is added in excess of the amount that can be incorporated in the surfactant structure, the excess is dispersed as droplets which are prevented from separating by the surfactant structure, thus the aliphatic oil and biocidal or agrochemical active substance are co-suspended by the structured surfactant. We have discovered that a significant reduction of the problems of loss of stability and/or mobility encountered with conventional oil-in-water suspensions in which structured surfactant is absent is provided by the present invention.

Our invention provides a suspension comprising; an aqueous structured surfactant; particles or droplets of a substantially water insoluble or sparingly soluble biocidal or agrochemical active substance in a weight ratio of total surfactant to said active substance of less than 20:1, suspended in said structured surfactant; and an aliphatic oil at least partially incorporated into the surfactant structure. In particular our invention provides such suspensions which comprise: water; sufficient surfactant to be able to provide a solid-suspending structure; sufficient dissolved surfactant-desolubilising electrolyte to form said structure; and from 2 to 40% by weight of an aliphatic hydrocarbon or glyceride oil, at least partially incorporated in said structure.

Preferably the product may be a lamellar structure such as those described in GB-2 123 846 or most preferably a spherulitic structure such as those described in GB-A-2 153 380.

Surfactants

The compositions of our invention preferably contain at least 3%, more usually at least 6%, e.g. at least 8% by weight of surfactants. The surfactants usually constitute up to about 35% by weight of the composition, although we prefer on economic grounds to use lower concentrations e.g. less than 30%, more usually less than 25%, preferably less than 20%, e.g. 10% to 15% by weight. It is, in theory possible to user higher surfactant concentration e.g. up to 60% or 70%, but such high levels are unlikely to be commercially justified and may cause technical problems of viscosity.

The surfactant may for example consist substantially of an at least sparingly water-soluble salt of sulphonic or mono esterified sulphuric acids e.g. an alkylbenzene sulphonate, alkyl sulphate, alkyl ether sulphate, alkyl ether sulphonate, olefin sulphonate, alkane sulphonate, alkylphenol sulphate, alkylphenol ether sulphate, alkylethanolamide sulphate, alkylethanolamide ether sulphate, or alpha sulpho fatty acid or its esters each having at least one alkyl or alkenyl group with from 8 to 22, more usually 10 to 20, aliphatic carbon atoms.

Said alkyl or alkenyl groups are preferably straight chain primary groups but may optionally be secondary, or branched chain groups. The expression "ether" hereinbefore refers to oxyalkylene and homoand mixed polyoxyalkylene groups such as polyoxyethylene, polyoxypropylene, glyceryl and mixed polyoxyethylene-oxypropylene or mixed glyceryl-oxyethylene, glyceryl-oxypropylene groups, or glyceryl-oxyethylene-oxypropylene groups, typically containing from 1 to 20 oxyalkylene groups. For example, the sulphonated or sulphated surfactant may be sodium dodecyl benzene sulphonate, potassium hexadecyl benzene sulphonate, sodium dodecyl dimethyl benzene sulphonate, sodium lauryl sulphate, sodium tallow sulphate, potassium oleyl sulphate, ammonium lauryl monoethoxy sulphate, or monethanolamine cetyl 10 mole ethoxylate sulphate.

Other anionic surfactants useful according to the present invention include fatty alkyl sulphosuccinates, fatty alkyl ether sulphosuccinates, fatty alkyl sulphosuccinamates, fatty alkyl ether sulphosuccinamates, acyl sarcosinates, acyl taurides, isethionates, soaps such as stearates, palmitates, resinates, oleates, linoleates, rosins soaps and alkyl ether carboxylates and saponins. Anionic phosphate esters including naturally occurring surfactants such as lecithin may also be used. In each case the anionic surfactant typically contains at least one aliphatic hydrocarbon chain having from 8 to 22 preferably 10 to 20 usually an average of 12 to 18 carbon atoms, an ionisable acidic group such as a sulphoacid, sulphate, carboxy, phosphono-or acid phosphate group, and, in the case of ethers, one or more glyceryl and/or from 1 to 20 ethyleneoxy and/or propyleneoxy groups.

Preferred anionic surfactants are sodium salts. Other salts of commercial interest include those of potassium, lithium, calcium, magnesium, ammonium, monoethanolamine, diethanolamine, triethanolamine and alkyl amines containing up to seven aliphatic carbon atoms, e.g. isopropylamine.

The surfactant may optionally contain or consist of nonionic surfactants. The nonionic surfactant may be e.g. a $C_{10-22}$ alkanolamide of a mono or di- lower alkanolamine, such as coconut or tallow monoethanolamide or diethanolamide. Other nonionic surfactants which may optionally be present, include ethoxylated alcohols, ethoxylated carboxylic acids, ethoxylated amines, ethoxylated alkylolamides, ethoxylated alkylphenols, ethoxylated glyceryl esters, ethoxylated sorbitan esters, ethoxylated phosphate esters, and the propoxylated, butoxylated and mixed ethoxy/propoxy and/or butoxy analogues of all the aforesaid ethoxylated nonionics, all having a $C_{8-22}$ alkyl or alkenyl group and up to 20 ethyleneoxy and/or propyleneoxy and/or butyleneoxy groups, or any other nonionic surfactant which has hitherto been incorporated in powder or liquid detergent compositions e.g. amine oxides. The latter typically have at least one $C_{8-22}$, preferably $C_{10-20}$ alkyl or alkenyl group and up to two lower (e.g. $C_{1-4}$, preferably $C_{1-2}$) alkyl groups.

The preferred nonionics for our invention are for example those having an HLB range of 6–18 e.g. 8–12.

Our compositions may contain cationic surfactants, which include quaternary amines having at least one long chain (e.g. $C_{12-22}$ typically $C_{16-20}$) alkyl or alkenyl group optionally one benzyl group and the remainder of the four substituents short chain (e.g. $C_{1-4}$) alkyl groups.

They also include imidazolines and quaternised imidazolines having at least one long chain alkyl or alkenyl group, and amido amines and quaternised amido amines having at least one long chain alkyl or alkenyl group. The quaternised surfactants are all usually salts of anions which impart a measure of water solubility such as formate, acetate, lactate, tartrate, chloride, methosulphate, ethosulphate, sulphate or nitrate.

Compositions of our invention may also contain one or more amphoteric surfactant, which include betaines, sulphobetaines and phosphobetaines formed by reacting a suitable tertiary nitrogen compound having a long chain alkyl or alkenyl group with the appropriate reagent, such as chloroacetic acid or propane sulphone.

Examples of suitable tertiary nitrogen containing compounds include: tertiary amines having one or two long chain alkyl or alkenyl groups and optionally a benzyl group, any other substituent being a short chain alkyl group; imidazolines having one or two long chain aikyl or alkenyl groups and amidoamines having one or two long chain alkyl or al kenyl groups.

The specific surfactant types described above are only exemplary of the commoner surfactants suitable for use according to the invention. Any surfactant capable of forming a structured system may be included. A fuller description of the principal types of surfactant which are commercially available is given in "Surface Active Agents and Detergents" by Schwartz Perry and Berch.

Electrolyte

Dissolved electrolyte compounds are strongly preferred constituents of our compositions. For the purposes of this Specification "electrolyte" means any water soluble, ionisable, non-surface-active compound which tends to desolubilise or "salt out" surfactants from solution or micellar solution.

Although it is possible to prepare structured systems in the absence of electrolyte, if the surfactant concentration is sufficiently high, the mobility of such systems is often insufficient unless the surfactant has been selected with great care. Addition of electrolyte permits the preparation of mobile structured systems containing relatively low concentrations of surfactant.

The electrolyte may be present in concentrations up to saturation. Typically the less the amount of surfactant present, the more electrolyte will be required to form a structure capable of supporting solid materials. We generally prefer to use higher concentrations of electrolyte and lower concentrations of surfactant, and to select the cheapest electrolytes on economic grounds. Thus electrolyte should normally be present in a concentration of at least 1% by weight based on the total weight of the composition, more usually at least 2% e.g. more than 3% preferably more than 4% especially more than 5%. Usually the concentration is less than 30% more usually less than 20% e.g. less than 15% by weight. Typically the concentration is between 5 and 12%.

The maximum electrolyte concentration depends, among other things, on the type of structure, and the viscosity required as well as considerations of cost. We prefer to form spherulitic systems as described in our application GB-A-2,153,380 in order to obtain a satisfactory balance between mobility and high payload of suspended agrochemicals. The optimum concentration of electrolyte for any particular type and amount of surfactant may be ascertained as described in our aforesaid application by observing the variation of electrical conductivity with increasing electrolyte concentration until the first conductivity minimum is observed. Samples may be prepared and tested by centrifuging for 10 minutes at 20,000 G, adjusting the electrolyte concentration to obtain a suspending medium which does not separate into two phases in the centrifuge. Preferably the electrolyte concentration is adjusted to provide a composition which is non-sedimenting on standing for three months at ambient temperature, or at 0° C. or 40° C.

Preferably also the electrolyte content is adjusted to provide a shear stable composition e.g. after shearing in a high shear mixer and, desirably, one which does not increase viscosity substantially after exposure to normal shearing, e.g. in a stirred tank.

Alternatively sufficient electrolyte may be added to form a lamellar system as described in GB-2,123,846, e.g. by adding enough electrolyte to ensure that the liquid suspending medium separates on centrifuging at 800 G for seventeen hours to form a lye phase containing little or no surfactant, and maintaining the dry weight at a value greater than the minimum at which the composition is non-sedimenting but below the maximum at which it is pourable. The amount of water in the formulation may be adjusted to obtain an optimum balance of mobility and stability.

In addition to cost, choice of electrolyte may depend on the intended use of the suspension. Fungicidal or pesticidal suspensions intended for crop protection preferably contain non-phytotoxic electrolytes, or concentrations insufficiently high to give rise to crop damage. Herbicidal compositions may contain auxiliary or synergistic herbicides as the electrolyte or part thereof. The selected electrolyte should also be chemically compatible with the solid to be suspended. Typical electrolytes for use in the present invention include alkali metal, alkaline earth metal, ammonium or amine salts including chlorides, bromides, iodides, fluorides, orthophosphates, condensed phosphates, phosphonates, sulphates, bicarbonates, carbonates, borates, nitrates, chlorates, chromates, formates, acetates, oxalates, citrates, lactates, tartrates, silicates, hypochlorites and, if required to adjust the pH, e.g. to improve the stability of the suspended solid or dispersed liquid or lower the phytotoxicity, acids or bases such as hydrochloric, sulphuric, phosphoric, citric or acetic acids, or sodium, potassium, ammonium or calcium hydroxides, or alkaline silicates.

It may be convenient to select plant nutrients as, or as part of, the electrolyte e.g. nitrates, potash and/or phosphates. Electrolytes which form insoluble precipitates with the surfactants or which may give rise to the formation of large crystals e.g. more than 1 mm on standing are preferably avoided. Thus for example concentrations of sodium sulphate close to its saturation concentration in the composition at normal room temperature, are undesirable. We generally prefer that sulphate concentration should be less than 3% more preferably less than 2% most preferably less than 1%.

Suspended Active Substance

The suspended biocidal or agrochemical active substance may comprise one or more agrochemicals or biocides such as selective or broad spectrum herbicides, defoliants, insecticides, miticides, moluscicides, nematicides and other vermicides, fungicides, bactericides, viricides and other pesticides, plant nutrients or growth or development regulators.

The particle or droplet size of the suspended material may vary widely. The maximum size that can be stably suspended depends upon the density of the suspended phase and the Yield Point of the suspending medium. However, for practical purposes we prefer that the maximum particle size is less than 1 mm, preferably less than 500 microns. Most preferably the mean particle size and majority of the particles are in the range 0.1 to 250 microns e.g. 0.5 to 200 especially 0.5 to 20 microns. Often the mean particle size is between 0.5 and 10 microns.

Where the active substance is a low melting solid, it is sometimes desirable to incorporate a small amount of a melting point depressant to inhibit phase changes during manufacture or storage of the composition. Such changes may give rise to instability.

Examples of suitable active substances include atrazine, alachlor, ethofumesate, phenmedipham, dazomet, mancozeb, methylene bis thiocyanate, amitraz, triforine, dimethoate, flusilazol, atkatox and pyridaphenthion.

The proportion of the suspended phase can vary widely between about 1% by weight and about 80% by weight but most commonly lies between 10 and 60%. In general it is preferred on economic grounds to suspend as much agrochemical as can be accommodated without loss of mobility, eg 30 to 50%. The viscosity of the suspensions at 21 $\sec^{-1}$ shear is typically between 0.2 and 50 Pascal seconds e.g. 0.2 to 5 Pascal seconds, preferably 0.2 to 3 Pascal seconds, especially 0.2 to 1.5 Pascal seconds. In general we prefer that the viscosity of the suspension measured at 136 $\sec^{-1}$ should be in the range of 0.05 to 10 Pascal seconds, preferably 0.08 to 5 Pascal seconds e.g. 0.1 to 2 Pascal seconds most preferably 0.15 to 1 Pascal seconds.

Aliphatic Oil

The alphatic oil may be a hydrocarbon oil such as a paraffin oil, e.g. kerosene or petroleum ether, or a terpenic oil such as limonene or citronellene. Alternatively, and preferably, the aliphatic oil is a glyceride, e.g. a vegetable oil such as olive oil, sunflower oil, rape seed oil, maize oil, palm oil, castor oil or jojoba oil.

The aliphatic oil may be entirely incorporated in the surfactant structure. For example, when the composition is spherulitic, the oil is incorporated in the structure of the spherulites, presumably as part of the concentric surfactant bilayers from which the spherulites are built up. However, an excess of oil may be tolerated, the excess forming separate oil droplets emulsified or suspended in the composition. Preferably the total amount of oil incorporated into the spherulites and suspended thereby is not greater than can be tolerated without substantial loss of stability or mobility of the suspension.

The maximum amount of oil that can be incorporated depends upon the particular surfactant system. Typically we prefer to include up to 35%, more preferably 3 to 30% e.g. 14 to 25% especially 15 to 20% of oil, based on the total weight of the composition.

Crystal Growth and Stability

One problem which arises with many suspensions of biocidal or agrochemical active substances in water is lack of stability due to interaction between the suspended agrochemical and the aqueous medium and/or other components of the formulation. For instance suspensions of amitraz present severe problems of crystal growth, arising from its slight solubility in the aqueous medium, while many pairs of agrochemicals which act synergistically or complementarily when applied to crops are chemically incompatible when stored together in aqueous concentrates.

Agrochemicals encapsulated in water soluble encapsulants such as water soluble film-forming polymers, may be stably suspended in aqueous structured liquids and retain their activity to a substantial degree on storage.

Encapsulation in water soluble film forming polymers and gums is a well known technique for binding a wide variety of sensitive ingredients, including pharmaceuticals and enzymes, and protecting them from deterioration during storage in air. Such capsules are conventionally used in an aqueous medium, which dissolves the capsule and releases the active ingredient immediately prior to use. It is not, therefore, on the face of it, possible to use such capsules to afford protection on storage in aqueous media.

We believe that the surprising stability of water soluble capsules in structured liquids is due to the relatively high electrolyte content of the latter. Electrolyte is required to interact with surfactants, which usually form a spherulitic or lamellar structure capable of suspending insoluble particles.

The suspending properties of a structured liquid detergent assist in preventing the protected agrochemical from undergoing agglomeration and sedimentation. We believe the electrolyte also prevents the dissolution of the water soluble capsules. The latter protect the agrochemicals until the formulation is diluted for use, when the electrolyte is diluted sufficiently for the capsule to dissolve and release the agrochemical.

Where the encapsulant is solid at normal ambient temperatures or can be absorbed in solid granules, the encapsulated agrochemical may be formed for example by granulation or prilling. Granules of agrochemical in a fluid bed or pan granulator may be coated with molten encapsulant or with a concentrated aqueous solution of the encapsulant which is evaporated to leave an encapsulating film. Alternatively fine particles of agrochemical dispersed in molten or aqueous encapsulant may be prilled or spray dried, respectively, to form fine, encapsulated particles. Such technology is already well known. One disadvantage of coating or prilling, however, is that difficulties are sometimes encountered obtaining perfect encapsulation. Any interruption in the integrity of the coating can cause coated agrochemical granules to deteriorate rapidly when added to aqueous suspending media.

The water soluble encapsulant for use according to our invention may be a water soluble film-forming organic macromolecule such as a polymer or gum. We particularly prefer a water soluble polyvinyl pyrrolidone. We can also use a polyvinyl alcohol, a cellulose derivative such as carboxymethyl cellulose, methyl cellulose, or hydroxypropylcellulose, a gum such as guar gum, gum benzoin, gum tragacanth, gum arabic or gum acacia, a protein such as casein, gelatin or albumin, a phospholipid such as lecithin, a carbohydrate such as starch, dextrose, galactose, or amylose, an amylopectin, or polycarboxyl ates such as polyacryl ates or polymal eates. The encapsulant is preferably not a surfactant or poly glycol.

The water soluble encapsulant is preferably a water soluble polymer that is precipitated by electrolyte, to form a solid gelatinous or viscous film or coherent layer surrounding the agrochemical particles. The solution of the encapsulant may conveniently have a concentration of from 0.5% by weight of encapsulant based on the weight of the solution up to saturation.

Where a polymer such as, for example, polyvinyl pyrrolidone is used as the encapsulant we prefer to use a polymer with a molecular weight of from 10,000 to 1,500,000 e.g. 15,000 to 1,000,000 more preferably 20,000 to 900,000, especially 25,000 to 800,000. In the case of polyvinyl alcohol we particularly prefer polymers with a molecular weight of 18,000 to 140,000 preferably 50,000 to 120,000 e.g. 80,000 to 100,000. Preferably any polyvinylalcohol used according to our invention is a partially hydrolysed polyvinyl ester of a lower (e.g. $C_1$ to 4) carboxylic acid, especially polyvinyl acetate, which has a degree of hydrolysis of greater than 25%, and desirably less than 95% especially 50 to 90% more preferably 60 to 80% e.g. 70% to 75%.

It is also possible to encapsulate particles of agrochemicals in hydrophobic liquids such as silicone oil, petroleum jelly or petroleum bright stock which are insoluble in aqueous surfactant. Such hydrophobic encapsulants may be preferred for certain pesticides whose retention and activity on leaves may be enhanced by the presence of hydrophobic liquid medium.

Solid or liquid agrochemicals may be dispersed in a hydrophobic liquid such as silicone oil and the dispersion itself dispersed in the aqueous surfactant medium.

The encapsulated agrochemical system preferably has a mean particle size in the range 2µ to 2.5 mm especially 5µ to 1 mm desirably 10µ to 700µ, more desirably 100µ to 500µ. We particularly prefer to disperse particles in the range 100 to 350µ.

The protected particles typically comprise from 0.5 to 90% by weight of encapsulant based on the weight of the particle, preferably 1 to 50% eg 2 to 20%.

Stability may also be affected by agglomeration or similar interaction between suspended crystallites. This may be avoided by use of steric inhibitors such as polyelectrolytes or similar dispersants which inhibit or prevent particle aggregation. For instance a minor proportion e.g. from 0.1 to 10% preferably 0.25 to 5% especially 0.5 to 3% by weight, of for example, lignin sulphonate, naphthalene sulphonate, polyvinyl alcohol, poly acrylate or maleic anhydride copolymer may be used.

Other Ingredients

We prefer that the suspensions of our invention should have low foaming properties. While this can be achieved by selecting inherently low foaming surfactants, we generally prefer to include antifoams such as silicone oil antifoams, phosphate esters, fatty alcohols or hydrocarbon oils. Typically the antifoam is required in concentrations of 0.1 to 5% by weight.

The composition may optionally include a suspending agent such as carboxymethyl cellulose or polyvinyl pyrrolidone, e.g. in amounts of from 0.1 to 5% preferably 0.5 to 2% by weight.

The composition may also, optionally, contain synergists, soluble biocides, plant nutrients, plant growth regulators, preservatives, buffers, antifreezes, colouring, and fragrances.

We prefer that the composition does not contain any volatile organic solvents, either water miscible solvents such as lower mono or polyhydroxy alchols, ketones and polyethers or water-immiscible solvents such aromatic hydrocarbons, nor any hydrotropes such as urea, benzene sulphonate or lower alkyl benzene sulphonates.

Solvents and hydrotropes tend to interfere with surfactant structuring and require the use of substantially increased amounts of surfactant and/or electrolyte. They also increase the cost of the formulation without generally increasing performance. Aromatic solvents are in addition undesirable on toxicity grounds.

We therefore prefer, if present at all, that solvents and hydrotropes are each present in proportions less than 10%, more preferably less than 5%, most preferably less than 1%, e.g. less than 0.5%, usually less than 0.1% and most commonly less than 0.05% by weight.

We similarly prefer that polymeric thickening agents such as gums are absent or present in concentrations less than 5%, preferably less than 0.5% since they are not generally necessary to stabilise the compositions and since they increase the cost and viscosity of the suspensions.

The invention will be illustrated by the following examples in which all percentages are by weight based on total weight.

Example 1

A suspension was made up from:

| | |
|---|---|
| Triethanolamine salt of $C_{10-12}$ alkyl benzene sulphonic acid (70% w/w aqueous solution) | 16.76% |
| Oleic Acid | 5.03% |
| Silicone defoamer (Union Carbide SILWET 7001) | 0.2% |
| Toxicant | 16.0% |
| Water | to 100% |

Example 2

A suspension was made up from:

| | |
|---|---|
| Isopropylamine salt of dodecyl benzene sulphonic acid (YS 94) | 3.94% |
| Nonyl phenol condensed with 9 moles of ethylene oxide (EMPILAN NP9) | 9.2% |
| Rape seed oil | 14.7% |
| Sodium methylnaphthalene sulphonic acid/formaldehyde concentrate (PL91.267) | 0.75% |
| Citric acid | 0.37% |
| Silicone defoamer (WACKER S132) | 0.06% |
| $NH_4H_2PO_4$ | 2.7% |
| Toxicant | 16.0% |
| Water | to 100% |

Example 3

A suspension was made up from:

| | |
|---|---|
| YS 94 | 4.05% |
| Isotridecanol condensed with 8 moles of ethylene oxide (DEHSCOXID 732) | 9.47% |
| Rape seed oil | 14.5% |
| PL91.267 | 0.77% |
| Citric acid | 0.23% |
| WACKER S132 | 0.06% |
| $NH_4H_2PO_4$ | 2.2% |
| Toxicant | 16.0% |
| Water | to 100% |

Example 4

A suspension was made up from

| | |
|---|---|
| YS94 | 12.6% |
| PL91.267 | 1.09% |
| Olive oil | 25.2% |
| Citric acid | 0.17% |
| WACKER S132 | 0.08% |
| Toxicant | 16.0% |
| Water | to 100% |

What is claimed is:

1. A biocidal or agrochemical composition consisting essentially of particles or droplets of a substantially water-insoluble or sparingly-soluble biocidally- or agrochemically-active substance cosuspended, by an aqueous structured surfactant, with an aliphatic oil, wherein the weight ratio of said surfactant to said active substance is less than 20:1, and said composition comprises between 3% and 40% by weight of said oil.

2. The composition of claim 1 wherein said composition comprises from 3% to 5% of said oil.

3. The composition of claim 2, in which the biocidally- or agrochemically-active substance is one selected from the group consisting of selective herbicides, broad-spectrum herbicides, defoliants, insecticides, miticides, molluscicides, nematicides or other vermicides, fungicides, bactericides, virucides or other pesticides, plant nutrients, growth regulators and development regulators; and said aliphatic oil is a hydrocarbon or glyceride oil.

4. A biocidal or agrochemical composition consisting essentially of particles or droplets of a substantially water-insoluble or sparingly-soluble biocidally- or agrochemically-active substance cosuspended, by an aqueous structured surfactant, with an aliphatic oil, wherein the weight ratio of said surfactant to said active substance is less than 20:1, and said composition comprises between 5% and 40% by weight of said oil.

5. The composition of claim 4, in which said surfactant is an anionic surfactant.

6. The composition of claim 4 containing from 5% to 35% by weight of said surfactant.

7. The composition of claim 4, wherein said percentage of surfactant is from 5% to 25% by weight.

8. The composition of claim 7, wherein said percentage of surfactant is from 6% to 8% by weight.

9. The composition of claim 7, wherein said percentage of surfactant is from 10% to 15% by weight.

10. The composition of claim 4, in which the biocidally- or agrochemically-active substance is one selected from the group consisting of selective herbicides, broad-spectrum herbicides, defoliants, insecticides, miticides, molluscicides, nematicides or other vermicides, fungicides, bactericides, virucides or other pesticides, plant nutrients, growth regulators and development regulators.

11. The composition of claim 10, in which said active substance has a particle size in the range 0.1 microns to 250 microns.

12. The composition of claim 11, in which said active substance has a particle size in the range 0.5 microns to 20 microns.

13. The composition of claim 12, in which said active substance has a particle size in the range 0.5 microns to 10 microns.

14. The composition of claim 4, in which said aliphatic oil is a hydrocarbon or glyceride oil.

15. The composition of claim 14, wherein said aliphatic oil is a hydrocarbon oil selected from the group consisting of paraffin oil and terpenic oils.

16. The composition of claim 15 containing at least one steric inhibitor selected from the group consisting of lignin sulphonate, naphthalene sulphonate, polyvinyl alcohol, polyacrylate and maleic anhydride copolymer; and 0.1% to 5% by weight of a suspending agent selected from the group consisting of carboxymethyl cellulose and polyvinyl pyrrolidone.

17. The composition of claim 4, in which the concentration of said oil is between 5.03% and 40% by weight.

18. The composition of claim 4, in which the concentration of said oil is from 14% to 25% by weight.

19. The composition of claim 18, in which the concentration of said oil is from 15% to 20% by weight.

20. The composition of claim 4, further containing from 0.1% to 5% of an antifoaming agent.

21. The composition of claim 20, in which said antifoaming agent is selected from the group consisting of silicone-based materials, phosphate esters and fatty alcohols.

22. The composition of claim 4, further containing from 0.1% to 5% by weight of a suspending agent.

23. The composition of claim 22, in which said suspending agent is selected from the group consisting of carboxymethyl cellulose and polyvinyl pyrrolidone.

* * * * *

UNITED STATES PATENT AND TRADEMARK OFFICE
CERTIFICATE OF CORRECTION

PATENT NO.   : 5,547,918
DATED        : August 20, 1996
INVENTOR(S)  : NEWTON et al It is certified that error appears in the above-indentified patent and that said Letters Patent is hereby corrected as shown below:

Title Page, Left Column, the following should be inserted:

--[73] Assignee: Albright & Wilson Limited,
                 West Midlands, England--.

Title Page, Right Column, Under FOREIGN PATENT
DOCUMENTS: after "2123294", "2/1994"
           should be --2/1984--.

Signed and Sealed this

Sixteenth Day of December, 1997

Attest:

BRUCE LEHMAN

Attesting Officer

Commissioner of Patents and Trademarks